United States Patent [19]

Murakami et al.

[11] Patent Number: 5,354,838
[45] Date of Patent: Oct. 11, 1994

[54] BLOOD SEPARATION COMPOSITION

[75] Inventors: Kazunori Murakami, Kusatsu; Tetsuo Taguchi, Yao, both of Japan

[73] Assignees: Nissho Corporation, Osaka; Hokoku Oil Mill Co., Ltd., Yao, both of Japan

[21] Appl. No.: 93,994

[22] Filed: Jul. 21, 1993

Related U.S. Application Data

[63] Continuation of Ser. No. 904,279, Jun. 25, 1992, abandoned.

[30] Foreign Application Priority Data

Jun. 25, 1991 [JP] Japan ................... 3-153237

[51] Int. Cl.$^5$ ............................................. C08G 63/16
[52] U.S. Cl. ....................... 528/272; 524/233; 524/240; 525/420.5; 528/295.3; 528/295.5; 528/296; 528/300; 528/302
[58] Field of Search ........................ 524/233, 240; 528/295.3, 295.5, 296, 300, 302, 272; 525/420.5

[56] References Cited

U.S. PATENT DOCUMENTS

| | | | |
|---|---|---|---|
| 4,101,422 | 7/1978 | Lamont et al. | 210/84 |
| 4,148,764 | 4/1979 | Lamont et al. | 260/22 |
| 4,462,926 | 2/1984 | Prater et al. | 528/295.5 |
| 5,124,434 | 6/1992 | O'Brien | 528/295.5 |

FOREIGN PATENT DOCUMENTS

| | | |
|---|---|---|
| 0075119 | 3/1983 | European Pat. Off. |
| 0076051 | 4/1983 | European Pat. Off. |
| 0384331 | 8/1990 | European Pat. Off. |
| 9108246 | 6/1991 | PCT Int'l Appl. |

*Primary Examiner*—Paul R. Michl
*Assistant Examiner*—Olga Asinovsky
*Attorney, Agent, or Firm*—Armstrong, Westerman, Hattori, McLeland & Naughton

[57] ABSTRACT

A blood separation composition for use in blood collection tubes. The composition comprises, as a gel-like material that is the main ingredient or the composition, a copolymer of sebacic acid with 2,2-dimethyl-1,3-propanediol and 1,2-propanediol. The separation composition may further comprise a thixotropic agent blended with the copolymer. The copolymer renders the blood separation composition stable and less flowable during storage, allowing it to form a stable partition barrier in each collection tube when centrifuged. The blood cells above the barrier are prevented from remaining within the serum, without any amount of harmful oily substances being released from the separation composition.

9 Claims, No Drawings

BLOOD SEPARATION COMPOSITION

This application is a continuation of application Ser. No. 07/094,279 filed Jun. 25, 1992, abandoned.

BACKGROUND OF THE INVENTION

1. Field of the Invention

The present invention relates to a blood component-separating composition (hereinafter referred to as "blood separation composition") which is employed in a centrifugal separation method to separate serum or plasma from whole blood, wherein the difference in specific gravity between them is utilized.

2. Prior Art

Many kinds of blood separation compositions which have been proposed are useful in the centrifugal method of blood separation. Those prior art separation compositions contain as their main ingredient a gel-like material such as silicone oil, a chlorinated poly-butane, an acrylic polymer or a copolymer of an α-olefin and a diester of maleic acid. Typical additives blended with the main ingredient are a thixotropic agent for enhancing important properties of the gel-like material; and an inorganic substance. The thixotropic agent causes the gel-like material not to flow within the blood collection tubes but to stay on bottom of the tubes while being transported. When centrifugal force is applied to the collection tubes filled with blood, the gel-like material moves upwards and forms a partition barrier between the serum (or plasma) and the clot. The thixotropic agent also enhances the strength and stability of the partition barrier. On the other hand, an inorganic substance such as titanium dioxide and calcium carbonate is blended with the gel-like material so as to adjust its specific gravity.

However, the prior art gel-like materials are disadvantageous in that it is not easy to adjust the viscosity and specific gravity to the levels desirable for a blood separation composition. Consequently, it has been necessary to add to the gel-like material a large quantity of a thixotropic agent and/or a specific density-adjusting agent, with the former agent adjusting the thixotropic property of the blood separation composition. Thus, the actual specific gravity of the blood separation composition cannot be kept at a constant level but varies among production lots thereof and over the course of time. In addition, fractions of the separation composition are likely to be dispersed in the serum phase (or plasma phase) which will be obtained by the centrifugal separation of blood samples. Said fractions will form an oily substance which floats in the serum or plasma and is likely to clog the nozzles in an automatic analyzer. Further, because of insufficient strength of the partition barrier, perfect centrifugal isolation of the serum (or plasma) from the clot is not ensured. A number of blood cells will remain in the serum phase above the partition, thus impairing the separation accuracy.

SUMMARY OF THE INVENTION

An object of the present invention, therefore, is to provide a blood separation composition free from the aforementioned drawbacks of the prior art separation compositions.

The blood separation composition provided in the invention comprises, as the gel-like material, a copolymer of sebacic acid with 2,2-dimethyl-1,3-propanediol and 1,2-propanediol, the gel-like material being the main ingredient of the blood separation means.

THE PREFERRED EMBODIMENTS

The inventors have conducted research to achieve the object of the invention and found that the copolymer of sebacic acid with 2,2-dimethyl-1,3-propanediol and 1,2-propanediol as said main ingredient is effective to easily realize the specific gravity and viscosity levels desired for the blood separation composition. The blood separation composition has a high separating capability even though it does not contain a large amount of thixotropic agent or specific gravity-adjusting agent and is, therefore, of a higher practical value.

Now, the invention will be summarized below in more detail.

A copolymer of sebacic acid polymerized with 2,2-dimethyl-1,3-propanediol and 1,2-propanediol is the gel-like material contained as the principal ingredient in the blood separation composition in accordance with the present invention.

A copolymerization ratio of 1 mole of sebacic acid to 1.02–1.07 moles of a mixture of 2,2-dimethyl-1,3-propanediol and 1,2-propanediol is desirable in the invention. An amount of sebacic acid below 1 mole in 1 mole of the copolymer will bring about an undesirably low viscosity of the gel-like material, whereas an excessively large amount of said acid above 1 mole will raise the viscosity to an undesirable extent.

The ratio of 2,2-dimethyl-1,3-propanediol to 1,2-propanediol is preferably 0.85:0.15–0.75:0.25. If the former is contained at a lower ratio, then the specific gravity of said gel-like material will become too high, and will make it difficult to handle the material while a higher ratio of the former diol will produce an undesirably low specific gravity and will cause an undesirably high melting point which makes the material waxy.

The molecular weight of the copolymer should be 1,000–10,000 and more preferably 2,000–8,000. A molecular weight of less than 1,000 will decrease excessively both the viscosity and the specific gravity of the copolymer to an unacceptable degree, whereas a molecular weight greater than 10,000 will raise the viscosity and specific gravity to a level which is not adequate for the blood separation composition.

The preferred specific gravity of the copolymer is 1.035–1.055 and the preferred viscosity is 30,000–150,000 cP, at 25° C.

With a specific gravity below 1.035 and a viscosity lower than 30,000 cP, the blood separation composition is too mobile to stand still within the tubes when a gravitational force or the like is imparted to it during storage. More specifically, the separation composition in this case may move close to a rubber stopper sealing the open end of the previously evacuated blood collection tube, even if received therein initially so as to rest on the bottom thereof. Consequently, it will not only be mixed with and thus contaminate a centrifugally separated serum or plasma, but also will be left sticking to the rubber stopper, thus making it difficult to obtain a pure sample of serum or plasma. Such a separation composition will rise (or "ascend") from the bottom of the tube prematurely so that the partition barrier is formed too early to prevent the blood cells from completely sinking below the barrier. Thus, the blood cells remaining within the fraction above the barrier will impair its separating capability.

On the contrary, a specific gravity above 1,055 in combination with a viscosity higher than 150,000 will hinder the smooth rising of the separation means, thus also failing to enhance a desirable capability of separation. An excessively high viscosity will cause further disadvantages such as difficult handling and allocation of the separation composition to a number of collection tubes.

A thixotropic agent may be added to the blood separation composition so that its thixotropic property is easily controlled. Although any conventional thixotropic agents can be used, preferred ones are fatty acid amides (as described in our related United States patent application filed on evendate herewith), silica, clay and the like. The fatty acid amides are inert to blood, and a small amount of the amides may be blended with the gel-like material in order to improve the gel property needed for the blood separation composition to form a partition barrier. Any of fatty acid amides having 10–25 carbon atoms, or more preferably 16–18 carbon atoms per molecule, or any mixture thereof can be employed herein.

0.5–7 parts by weight, or more preferably 1–4 parts by weight, of the fatty acid amides can be added to 100 parts by weight of the copolymer.

In a case wherein fatty acid amide(s) as the thixotropic agent is added at a ratio falling within this range, the gel-like material will have a desirable flowability which improves the shape stability and storage stability of the material, thus providing a blood separation composition which is excellent in its "ascendability" and its partition strength.

The blood separation composition of the invention may readily be produced, for example, by conducting the steps of: heating a given amount of the gel-like material to a temperature between 60° C. and 80° C., i.e., the copolymer of sebacic acid with 2,2-dimethyl-1,3-propanediol and 1,2-propanediol; adding thereto an appropriate amount of the thixotropic agent, e.g., the fatty acid amide(s); and continuing to stir this mixture with sufficient shearing stress, while keeping the temperature, until the amide(s) is completely dissolved in the gel-like material.

The blood separation composition prepared in this manner according to the invention need have a specific gravity intermediate those of the serum or plasma and the clot. The separation composition when put into blood collection tubes usually rests on the bottom thereof. Therefore, a large difference in specific gravity between the separation means and the clot or blood cells is advantageous in that the centrifuged separation composition can ascend within the tubes more smoothly and more rapidly. On the other hand, a separation means which has an overall specific gravity of less than 1,035 includes fractions whose specific gravity is much lower than 1,035. These fractions may undesirably migrate from said composition into the centrifugally separated serum phase or plasma phase.

In addition to a specific gravity as prescribed above, the blood separation composition which is composed of the gel-like material and the predetermined amount of thixotropic agent preferably has a viscosity from 100,000 to 400,000 cP at 25° C. (when measured in the same manner as will be described for the Examples given below).

The specific gravity as well as the viscosity of the separation means can be adjusted, if necessary, by further adding an amount of an inorganic substance such as titanium dioxide or calcium carbonate.

EXAMPLES

The following Examples are given only by way of example, with no intention of delimiting thereto the scope of the present invention.

Viscosities described in the Examples were measured using an "E-Type Viscometer" which is a rotary viscometer (with a cone angle at 3° and a diameter of 28 mm, made by TOKYO KEIKI CO., LTD.). Specific gravities were measured according to the Cupric Sulfate Method using cupric sulfate solutions of different concentrations. One drop of each sample was put in the solutions, in order to find which of them neither caused the drop to rise to the surface nor sink to the bottom. The thus found solution ought to have the same specific gravity as the tested sample.

Preparation of Copolymers

Copolymer No.1

The copolymers of sebacic acid may be produced by any conventional method known in this field of art.

Polymerization was carried out in a four-mouthed flask comprising a stirrer, a thermometer, an $N_2$ gas-introducing tube and a Vigreaux column. This Vigreaux column of a medium length comprised in turn a distillation head and a condenser which was composed of a thermometer and a receptacle. The condenser was arranged to distill water and/or an amount of excessive diol, under atmospheric or reduced pressure. Reactants which were involved in this process are as follows.

202 grams of sebacic acid, 89 grams of 2,2-dimethyl-1,3-propanediol and 16 grams of 1,2-propanediol were put in the four-mouthed flask to thereby form a reaction mixture. This mixture was heated up to about 225° C., by continuously removing water therefrom while maintaining the vapor temperature almost constant to fall within a range of about 100°–120° C. Upon detection of a reduced rate of water generation after about 4 hours from the start of reaction, a small amount of a titanium compound as an esterification catalyst (at a ratio corresponding to 0.005% of the initial weight of the reactants) was added. At the same time, the reaction system pressure was reduced to 70–100 mmHg, and reaction was continued for 5 hours under this condition. Subsequent to this phase of the process, the pressure was reduced below 5 mmHg for a further reaction for 3 hours. A highly viscous product was discharged from the flask and cooled to room temperature to give a yield of 98%. This product's viscosity was 35,000 cP, and the specific gravity was 1.041 at 25° C., with its molecular weight being 3,800.

Copolymer No. 2

202 grams of sebacic acid, 87 grams of 2,2-dimethyl-1,3-propanediol and 15 grams of 1,2-propanediol were put in the four-mouthed flask to form another reaction mixture. Reaction to produce a copolymer was carried out in the same manner as for the copolymer No. 1, except that the total reaction time was 15 hours including the last phase for 3 hours with a pressure kept at 1.5 mmHg. The yield of copolymer No. 2 obtained in this manner was 95%, its viscosity being 150,000 cP with a specific gravity of 1.041 at 25° C., with its molecular weight being 6,600.

Copolymer No. 3

202 grams of sebacic acid, 88 grams of 2,2-dimethyl-1,3-propanediol and 16 grams of 1,2-propanediol were put in the four-mouthed flask to form still another reaction mixture. Reaction to produce a copolymer was carried out in the same manner as for the copolymer No. 1, except that the total reaction time was 15 hours including the last phase for 3 hours with a pressure kept at 1.5 mmHg. The yield of copolymer No. 3 obtained in this manner was 95%, its viscosity being 68,000 cP with a specific gravity of 1.041 at 25° C., with its molecular weight being 4,400.

Preparation of blood separation means

EXAMPLE No. 1

This example of the blood separation composition was prepared by blending 2 parts by weight of stearamide (containing a small mixed amount of palmitamide) with 100 parts by weight of the copolymer No. 1. The composition of Example No. 1 showed a viscosity of 140,000 cP and specific gravity of 1.043 at 25° C.

EXAMPLE No. 2

3 parts by weight of stearamide were blended with 100 parts by weight of the copolymer No. 1 to give Example No. 2 of a blood separation composition having a viscosity of 187,000 cP and a specific gravity of 1.042 at 25° C.

EXAMPLE No. 3

2 parts by weight of stearamide were blended with 100 parts by weight of the copolymer No. 2 to give Example No. 3 of a blood separation composition having a viscosity of 260,000 cP and a specific gravity of 1.041 at 25° C.

EXAMPLE No. 4

3 parts by weight of stearamide were blended with 100 parts by weight of the copolymer No. 3 to give Example No. 4 of blood a separation composition having a viscosity of 156,000 cP and a specific gravity of 1.042 at 25° C.

EXAMPLE No. 5

4 parts by weight of stearamide were blended with 100 parts by weight of the copolymer No. 3 to give Example No. 4 of a blood separation means having a viscosity of 187,000 cP and a specific gravity of 1.042 at 25° C.

Reference No. 1

0.01 parts by weight of stearamide were blended with 100 parts by weight of the copolymer No. 3 to give a reference example of a blood separation means having a viscosity of 80,000 cP and a specific gravity of 1.041 at 25° C.

Reference No. 2

10 parts by weight of stearamide were blended with 100 parts by weight of the copolymer No. 2 to give another reference example having a viscosity of 460,000 cP and a specific gravity of 1.044 at 25° C.

Reference No. 3

4 parts by weight of stearamide as well as 4 parts by weight of fine silica ("Aerosil R972", a trademark of Nippon Aerosil Co., Ltd.) were blended with 100 parts by weight of a copolymer of $\alpha$-olefin and maleic acid to prepare still another reference example having a viscosity of 360,000 cP and a specific gravity of 1.039 at 25° C.

Comparison of Examples with References

Example Nos. 1–5 as well as Reference Nos. 1–3 were tested for their stability during storage and their capability of dividing blood phases.

(1) Stability During Storage

Blood collection/separation tubes made of glass and those made of polyethylene terephthalate, having an inner diameter of 13.6 mm, were used. A small amount of a blood separation composition of an "Example" or "Reference" weighing 1.5 grams was put into each tube, and after being kept at 25° C. for 24 hours, the "flow distance" of said composition was measured at different temperatures. The "flow distance" is the distance between an initial position of the blood separation means and a final position thereof which was measured after predetermined hours of storage had passed. The results of this test are given in Table 1.

As will be seen from the data in the table, the blood separation composition of the present invention was more stable even if stored for a long time, and less flowable when transported or handled otherwise, than the blood separation compositions represented by the Reference examples.

TABLE 1

| Material of tube | Flow distance (mm) | | | |
|---|---|---|---|---|
| | Glass | | PET(*) | |
| Temperature and Period of Storage | 40° C. for 336 hr. | 60° C. for 72 hr. | 40° C. for 336 hr. | 60° C. for 72 hr. |
| Examples | | | | |
| No. 1 | 4 | 8 | 3 | 6 |
| No. 2 | 0 | 1 | 0 | 3 |
| No. 3 | 4 | 8 | 3 | 7 |
| No. 4 | 0 | 1 | 0 | 2 |
| No. 5 | 0 | 0 | 0 | 0 |
| References | | | | |
| No. 1 | 10 | 21 | 9 | 19 |
| No. 2 | 0 | 0 | 0 | 0 |
| No. 3 | 5 | 8 | 3 | 7 |

Notes:
"PET" = polyethylene terephthalate

(2) Capability of Dividing Blood Phases

Similarly, blood collection/separation tubes made of glass and/or polyethylene terephthalate, having an inner diameter of 13.6 mm, were used. A small amount of a blood separation composition of an "Example" or "Reference" weighing 1.7 grams was put into each tube, and kept therein at 25° C. for 24 hours after storage at 40° C. for 336 hours.

9 ml of human whole blood was put into each tube, and after complete coagulation thereof, the tubes were centrifuged at 1,300 G for 10 minutes ("G" being the gravitational acceleration).

Performance or capability of the blood separation compositions was evaluated as to the following items, according to the standards given below.

The term "ascendability" used herein indicates the extent to which the blood separation composition can rise in the centrifuged collection tube previously filled with a given amount of human blood. A rating symbol "+++" ('excellent') was allotted to the separation composition which completely rose within the blood collection tube, while another symbol "++" ('good') means a small amount of said composition remained on the tube bottom. A further rating symbol "+" ('poor') represents a significant amount of the blood separation composition which was left on the bottom, whereas a still further symbol "±" ('worse') denotes a quite unsatisfactory rising of the separation composition which fully remained on said tube bottom.

Further, the "stability of partition barrier" between the serum and the clot was judged based on the state of said barrier sticking to the tube wall, when 24 hours had passed after the centrifugal separation process. Similarly to the "rising" property, the rating symbols "+++" (excellent), "++" (good), "+" (poor) and "±" (worst) respectively indicate: the perfectly sticking barrier; partially loosened barrier; significantly loosened barrier; and thoroughly loosened barrier.

The "released amount of oily substance" from the separation means was inspected by observation of the serum surface.

"Reddishness" of the serum was checked to determine whether or not any significant number of blood cells had been left in the serum, and also to determine whether or not hemolysis had occurred.

Test results are given in Tables 2 and 3 respectively for the glass tubes and for the polyethylene terephthalate tubes.

It will be seen from the data of Tables 2 and 3 that in the blood phase-separating operation using the separation composition provided in the invention, not only ascendability but also stability of the partition barrier are excellent and satisfactory. Besides, there is observed neither any amount of oily substance released nor any extent of hemolysis or any number of blood cells remaining in the serum.

TABLE 2

| | Ascend-ability | Stability of partition | Oily substance released | Reddishness of serum |
|---|---|---|---|---|
| Examples | | | | |
| No. 1 | +++ | ++ | Null | No(*) |
| No. 2 | +++ | +++ | Null | No |
| No. 3 | +++ | ++ | Null | No |
| No. 4 | +++ | +++ | Null | No |
| No. 5 | ++ | +++ | Null | No |
| References | | | | |
| No. 1 | +++ | ± | Null | No |
| No. 2 | ± | +++ | Null | No |
| No. 3 | ± | ++ | Present | A little |

Notes:
"No" = no mixing of blood cells in serum
+++ = excellent
++ = good
+ = poor
± = worst

TABLE 3

| | Ascend-ability | Stability of partition | Oily substance released | Reddishness of serum |
|---|---|---|---|---|
| Examples | | | | |
| No. 1 | +++ | +++ | Null | No(*) |
| No. 2 | +++ | +++ | Null | No |
| No. 3 | +++ | +++ | Null | No |
| No. 4 | +++ | +++ | Null | No |
| No. 5 | ++ | +++ | Null | No |
| References | | | | |
| No. 1 | +++ | ± | Null | No |
| No. 2 | ± | +++ | Null | No |
| No. 3 | ± | ++ | Present | A little |

Notes:
"No" = no mixing of blood cells in serum
+++ = excellent
++ = good
+ = poor
± = worst It will now be apparent from the foregoing that the blood separation composition provided by the invention is advantageous in its high separating capability and its good stability which are not affected by a long storage period or the like. It does neither move adversely within the collection tubes during transportation thereof, nor change in its minimum shear stress and its rising property in the centrifugal process, thus maintaining its high capability of separating blood phases. Further, the separation composition is inert to blood so that blood is not absorbed nor is hemolysis caused by it. Radiation sterilization using gamma-rays or the like will not give rise to any physical or chemical change of the separation composition. Further, the separation composition will not release any oily substance which will give an undesirable influence to the operation of testing apparatuses.

What is claimed is:

1. A blood separation composition consisting essentially of, as a main ingredient thereof, a gel material which is a copolymer consisting of sebacic acid with 2,2-dimethyl-1,3-propanediol and 1,2-propanediol; and a thixotropic agent.

2. A blood separation composition as defined in claim 1, wherein a copolymerization ratio of sebacic acid to a total of 2,2-dimethyl-1,3-propanediol and 1,2-propanediol falls within a range from 1:1.02–1:1.07.

3. A blood separation composition as defined in claim 2, wherein a ratio of 2,2-dimethyl-1,3-propanediol to 1,2-propanediol is from 0.85:0.15–0.75:0.25.

4. A blood separation composition as defined in claim 1, 2 or 3, wherein the molecular weight of the copolymer is from 1,000–10,000.

5. A blood separation composition as defined in claim 4, wherein the molecular weight of the copolymer is from 2,000–8,000.

6. A blood separation composition as defined in claim 5, wherein the copolymer has a specific gravity of 1,035–1,055 and a viscosity of 30,000–150,000 cP at 25° C.

7. A blood separation composition as defined in claim 6, further comprising, as the thixotropic agent, 1–4 parts by weight of a fatty acid amide blended with 100 parts by weight of the copolymer, whereby the blood separation means has a viscosity of 100,000–400,000 cP at 25° C.

8. A blood separation composition as defined in claim 3, wherein the amount of 2,2-dimethyl-1,3-propanediol based on 1,2-propanediol is less than 0.85.

9. A blood separation composition consisting of a gel material which is a copolymer consisting of sebacic acid with 2,2-dimethyl- 1,3-propanediol and 1,2-propanediol, and a thixotropic agent.

* * * * *